United States Patent
Rodriguez

(10) Patent No.: US 9,295,692 B1
(45) Date of Patent: Mar. 29, 2016

(54) GEL-BASED COMPOSITIONS AND METHODS OF USE

(71) Applicant: Arcadio Maldonado Rodriguez, Colima (MX)

(72) Inventor: Arcadio Maldonado Rodriguez, Colima (MX)

(*) Notice: Subject to any disclaimer, the term of this patent is extended or adjusted under 35 U.S.C. 154(b) by 0 days.

(21) Appl. No.: 14/576,290

(22) Filed: Dec. 19, 2014

(51) Int. Cl.
| | |
|---|---|
| *A61K 31/78* | (2006.01) |
| *A61K 8/81* | (2006.01) |
| *A61K 8/60* | (2006.01) |
| *A61K 8/37* | (2006.01) |
| *A61K 8/19* | (2006.01) |
| *A61K 8/34* | (2006.01) |
| *A61K 8/36* | (2006.01) |
| *A61K 9/00* | (2006.01) |
| *A61Q 11/00* | (2006.01) |

(52) U.S. Cl.
CPC . *A61K 31/78* (2013.01); *A61K 8/19* (2013.01); *A61K 8/345* (2013.01); *A61K 8/36* (2013.01); *A61K 8/37* (2013.01); *A61K 8/60* (2013.01); *A61K 8/8152* (2013.01); *A61K 9/0014* (2013.01); *A61Q 11/00* (2013.01); *A61K 2800/70* (2013.01)

(58) Field of Classification Search
USPC ..................... 429/195.17; 514/547
See application file for complete search history.

(56) References Cited

U.S. PATENT DOCUMENTS

| | | | | |
|---|---|---|---|---|
| 8,420,699 | B1* | 4/2013 | Dubow | 514/547 |
| 2012/0195923 | A1* | 8/2012 | Turgeon et al. | 424/195.17 |

* cited by examiner

*Primary Examiner* — Walter Webb
(74) *Attorney, Agent, or Firm* — Benjamin A. Adler

(57) ABSTRACT

Provided herein are a biocompatible gels, such as an oral gel composition and a topical gel composition. Generally, the oral gel composition may comprise a formulation in ozonized water of a cross-linked polyacrylate polymer and a preservative and sodium hydroxide, acetic acid, and glycerol to polymerize the polyacrylate. Optionally, the oral gel composition may comprise a sweetener and/or a flavoring agent. The topical gel composition is a similar formulation in ozonized water with a cross-linked polyacrylate polymer and a preservative and sodium hydroxide, acetic acid, and hydrogen peroxide to polymerize the polyacrylate. Further provided are methods of using the gel compositions to reduce dental caries and to treat a skin injury.

8 Claims, No Drawings

GEL-BASED COMPOSITIONS AND METHODS OF USE

BACKGROUND OF THE INVENTION

1. Field of the Invention

The present invention relates generally to the fields of oral and topical pharmaceutical compositions or formulations. More specifically, the present invention relates to gel based oral or dental and topical or dermal pharmaceutical compositions and formulations and methods for their use.

2. Description of the Related Art

Oral health can be defined as the absence of acute or chronic orofacial pain, oral and throat cancer, oral sores, birth defects such as cleft lip or palate defects, periodontal disease, tooth decay, tooth loss, and other diseases and disorders that affect mouth. Oral diseases share risk factors with the four major chronic diseases that affect humans (cardiovascular diseases, cancer, chronic respiratory diseases and diabetes), as are favored by harmful diets, smoking and harmful alcohol consumption. Another risk factor is poor oral hygiene. The most common oral diseases are dental caries and periodontal range of dental caries which affects from 60% to 90% of the population.

Current products for oral hygiene in the market use primarily antibiotics and antimicrobial active ingredients to combat dental bacteria, sometimes referred to as dental "biofilms". While current products can provide a temporary antiseptic protective effect, adverse effects in the oral cavity and/or systemically can result. For example, chlorhexidine contraindications include use for prolonged periods of time and possible allergic reactions, as well as contraindications with other compounds such as sodium fluoride typically applied as a preventive cariogenic agent. Similarly, the antiseptic Triclosan is less toxic than chlorhexidine but is still undesirably toxic for prolonged use in patients.

Worldwide, it is considered that tooth loss is a natural consequence of aging, but in fact it is preventable. Dental caries is still a problem in developed countries affecting between 60% and 90% of the school population and the vast majority of adults. Tooth decay is the most prevalent oral disease in several Asian and Latin American countries.

Plaque-forming agents number some 700 etiologic microbial genera, including the bacterial flora *Streptococcus sanguis, Streptococcus mitis, Streptococcus oralis* and *Actinomyces naeslundii*. These microorganisms are precursors in the formation of dental plaque. Later, other bacteria proliferate such as *Streptococcus mutans, Streptococcus salivarius, Streptococcus gordonii, Streptococcus parasanguis, Neisseria* spp among others, affecting oral health significantly leading to periodontal diseases. The genesis of dental biofilm is a dynamic and complex process and is difficult to understand in its entirety.

Thus, there is a recognized need for an innovative strategy to protect dental organs and adjacent soft tissues in order to prevent the formation of dental biofilms. The present invention fulfills this longstanding need and desire in the art.

SUMMARY OF THE INVENTION

The present invention is directed to a biocompatible gel comprising a formulation of a polymerized biopolymer-ozonized water homogenate and a preservative. The present invention is directed to a related biocompatible gel further comprising a sweetener. The present invention is directed to another related biocompatible gel further comprising a flavoring agent.

The present invention also is directed to an oral gel composition. The oral gel composition comprises a formulation in ozonized water of cross-linked polyacrylate, trichloro-galactosucrose and methyl paraben, where the polyacrylate is polymerized in sodium hydroxide, acetic acid and glycerol. The present invention is directed to a related oral gel composition further comprising a flavoring agent.

The present invention is directed further to a topical gel composition. The topical gel composition comprises a formulation in ozonized water of cross-linked polyacrylate and methyl paraben, where the polyacrylate is polymerized in sodium hydroxide, acetic acid and hydrogen peroxide.

The present invention is directed further still to a method for reducing dental caries in a subject. The method comprises applying an amount of the oral gel composition described herein to teeth and gums of the subject effective to prevent the formation of biofilms thereon.

The present invention is directed further still to a method for treating an injury to skin on a subject. The method comprises applying an amount of the topical gel composition described herein to the injury thereby improving hemostasis of the injury and increasing analgesia in the subject.

Other and further aspects, features, and advantages of the present invention will be apparent from the following description of the presently preferred embodiments of the invention given for the purpose of disclosure.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

In one embodiment of the invention there is provided a biocompatible gel, comprising a formulation of a polymerized biopolymer-ozonized water homogenate and a preservative. Further to this embodiment the biocompatible gel comprises a sweetener. An example of a sweetener is trichloroglactosucrose. Further still to this embodiment the biocompatible gel comprises a flavoring agent. An example of a flavoring agent is mint.

In one aspect of these embodiments the biopolymer may be polymerized with sodium hydroxide, acetic acid and glycerol. In an alternative aspect, the biopolymer may be polymerized with sodium hydroxide, acetic acid and hydrogen peroxide.

In yet another aspect of these embodiments the biocompatible gel may be an oral formulation comprising ozonized water, a cross-linked polyacrylate polymer, sodium hydroxide, acetic acid, glycerol, a sweetener, a preservative, and a flavoring agent. In yet another aspect the the biocompatible gel may be a topical formulation comprising ozonized water, a cross-linked polyacrylate polymer, sodium hydroxide, acetic acid, hydrogen peroxide, and a preservative.

In all embodiments and aspects thereof, the biopolymer may be a cross-linked polyacrylate polymer. Also, in all embodiments and aspects the preservative may be methyl paraben.

In another embodiment of the present invention there is provided an oral gel composition comprising a formulation in ozonized water of cross-linked polyacrylate, trichloro-galactosucrose and methyl paraben, where the polyacrylate is polymerized in sodium hydroxide, acetic acid and glycerol.

In this embodiment the ozonized water may contain less than 20 µg/l of ozone. Also, the formulation may contain per liter of ozonized water about 35 g to about 45 g of the polyacrylate, about 45 g to about 55 g of the trichloro-galactosucrose, about 0.7 g to about 1.3 g of the methyl paraben, about 4.5 ml to about 5.6 ml of the sodium hydroxide, about 2.5 ml to about 3.5 ml of the acetic acid, and about 2.4 ml to about 3.2 ml of the glycerol. Further to this embodiment the oral gel composition may comprise a mint flavoring agent. Particularly, the formulation contains per liter of ozonized water about 4.5 g to about 5.5 g of the mint flavoring agent.

In yet another embodiment of the present invention there is provided a topical gel composition comprising a formulation in ozonized water of cross-linked polyacrylate, and methyl paraben, where the polyacrylate is polymerized in sodium hydroxide, acetic acid and hydrogen peroxide. In this embodiment the ozonized water is as described supra. Also, the formulation may contain per liter of ozonized water about 6.3 g to about 7.7 g of the polyacrylate, about 0.7 g to about 1.3 g of the methyl paraben, about 3.0 ml to about 3.7 ml of the sodium hydroxide, about 1.5 ml to about 2.5 ml of the acetic acid, and about 1.5 ml to about 2.5 ml of the hydrogen peroxide.

In yet another embodiment of the present invention there is provided a method for reducing dental caries in a subject, comprising the step of applying an amount of the oral gel composition as described supra to teeth and gums of the subject effective to prevent the formation of biofilms thereon.

In yet another embodiment of the present invention there is provided a method for treating an injury to skin on a subject, comprising the step of applying an amount of the topical gel composition as described supra to the injury thereby improving hemostasis of the injury and increasing analgesia in the subject.

Provided herein are oral compositions and formulations effective to prevent or reduce the formation of dental biofilms or bacteria on teeth. The oral dental gel compositions of the present invention have an extraordinary lingering effect as a barrier and is fully safe and nontoxic. In addition, the gel compositions of the present invention do not generate allergies, are low cost, i.e., about 10 to about 20 cents per application, and has excellent organoleptic properties in its taste, smell and appearance. The oral gel composition of the present invention has no antimicrobial effect per se, and therefore, does not affect the normal oral microbial flora, or generate resistant strains, but helps to prevent biofilm formation, and therefore the formation of dental plaque tartar and periodontal diseases.

As an oral gel composition, when applied to the teeth with a toothbrush, the formulation is such that the composition spontaneously and firmly adheres to the surface of dental organs and periodontal tissues and persists at least 72 hours. The dental gel provides a slippery film on its outer surface with a colorless and translucent face that prevents the sticking of food debris on the dental and periodontal bodies, while also sealing dental imperfections and cracks. Therefore, the formulation of the gel composition lacks the nutrients necessary for the growth of indigenous oral microbiota and prevents the formation of a plaque dentomicrobiana effect as no product on the market has demonstrated.

Another advantage of the oral gel composition of the present invention is its easy application regardless of the user's age and its lack of toxicity. The gel composition does not cause adverse reactions in the oral cavity because the components of the formulation comprise a biocompatible polymer, for example, a carbomer such as cross-linked polyacrylate polymer, dissolved in ozonized water and an artificial sweetener, for example, trichlorogalactosucrose, sodium hydroxide, glycerol, acetic acid, and methyl paraben. The oral formulation also may comprise a flavorant or flavoring agent, such as, but not limited to, mint. This oral formulation at least partially, preferably totally, modifies temporary indigenous microbial flora of the oral cavity unlike existing products known in the art and commercially available.

The formulation of the dental gel composition of the present invention can be applied one or more times per day to prevent the formation of dental biofilm, to reduce or prevent bad breath due to putrefaction of food waste, prevent tooth decay and periodontal disease and, therefore, to prevent daily bacteremia and systemic microbial conditions. Thus, methods of improving oral hygiene, such as, preventing or reducing the occurrence of biofilms or bacteria on the teeth also are provided.

The oral gel compositions of the present formulation provide a non-toxic formulation being substantially or almost completely safe and effective and useful for anyone regardless of his or her clinical, medical, psychosocial, and economic situation. For example, a 30 g tube of the oral gel composition (about 30,000 mg/60 mg per application per day) provides approximately 500 applications making it an affordable investment that improves oral hygiene and enhances the preservation of teeth.

Also provided are topical or dermal gel compositions effective for use on the skin. The components of the topical formulation are similar to those of the oral gel and, as with the oral gel, provide a non-toxic, safe and effective composition. For example, a dermal gel may comprise the biocompatible polymer of the oral gel dissolved in ozonized water, sodium hydroxide, acetic acid, hydrogen peroxide, and methyl paraben The topical gel compositions of the present invention have analgesic properties with many uses for, but not limited to, asepsis, dermal revitalization, topical analgesia and decreased skin-bleeding. Thus, the topical gel composition of the present invention is useful to treat, alleviate or provide analgesia for, but not limited to, sunburn, mild to moderate skin burns, dermal ulcers, abrasions, wounds, skin blemishes, and skin lacerations with or without loss of blood. Thus, methods of alleviating or treating a condition of the skin also are provided.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Preparation of Oral Gel Composition

To create one preferred formulation of the dental gel composition, to 7.5 liters of ozonized water at <20 ppb (<20 µg/l), 300 g of carbopol #940 is added. The carbopol-ozonized water is homogenized and allowed to stand for about 24 hours. Subsequently, the formulation is polymerized with 38 ml of sodium hydroxide (NaOH/5%), 20 ml of glycerol, 22.5 ml of acetic acid, 375.0 g of trichloro-galactosucrose, 7.5 g of methyl paraben and 37.5 ml of mint. 30 grams or 1 oz of oral gel composition is produced.

Thus, a preferred formulation of the oral gel composition of the present invention is: 1) ozonized water; 2) carbopol #940; 3) sodium hydroxide (NaOH); 4) glycerol; 5) acetic acid; 6) trichloro-galactosucrose; 7) methyl paraben; and 8) mint.

EXAMPLE 2

Study Design and Methodology

An intervention study of minimal risk to the health of the participating subjects was undertaken with a duration of 168 days (24 weeks), nominal data and scale-up of 3 cohorts or groups made up of ten subjects each, 1) Study Group, 2) Control 1 Group and, 3) Control 2 Group. This study was designed to show whether the use of the oral dental gel composition applied to dental organs of the participating study group was able to prevent the development of plaque and tartar dentomicrobiana compared to the development of plaque and tartar on dentomicrobiana groups Control 1 Group and Control 2 Group. To this end, 30 subjects of either sex and any age as a "healthy" population were enlisted (15 from the city of Colima and 15 from the city, Uriangato, Guanajuato) were informed of the minimum risk to subjects and of potential participation during follow-up in the event of conditions that endanger the health of the subject. The subjects read and signed the informed consent letter, endorsed with the name and signature of the parent or guardian responsible.

The study inclusion criteria were: satisfactory health, no antibiotic use or anti-inflammatory or steroidal drugs one month prior to or during the study, no use any form of chemical control of biofilm during the study period and consent and commitment to follow the directions in the study. All subjects recruited dentists to follow them for supragingival and subgingival cleaning and were assigned to each of the three groups by random lottery (subjects 1-10 are assigned to the treatment study group, subjects 11-20 were assigned to the Control 1 Group and subjects 21-30 are assigned to Control 2 Group.

In Study Group 1 for each subject the following was performed: a clinical evaluation, application of plaque disclosing tablet (all showed plaque and calculus), supragingival and subgingival cleaning, training for proper flossing, brushing techniques, and how the oral gel composition is applied.

In Control Group 1 for each subject the following was performed: a clinical evaluation, application of plaque disclosing tablet (all showed plaque and calculus), supragingival and subgingival cleaning, training for proper flossing and brushing techniques. No oral gel compositions of the present invention were applied.

In Control Group 2 for each subject the following was performed: a clinical evaluation, application of plaque disclosing tablet (all showed plaque and calculus) and supragingival and subgingival cleaning. No training in oral hygiene was provided nor was the oral gel composition applied.

Clinical evaluation for each of the subjects in Control Group 2 and application of a dental plaque disclosing tablet showed plaque and tartar. No action other than supragingival and subgingival cleaning was done.

The amount of the oral gel composition applied was about the size of two drops of water and distributed evenly with a toothbrush on all tooth surfaces and occlusal surfaces. Its properties allow firm adherence to the surfaces of dental organs, occlusal surfaces and adjacent soft tissue forming a protective film that prevents plaque formation with its clinical consequences.

The oral gel compositions have a mildly sweet taste, are non-irritating and can be used indefinitely as it is non-toxic and does not change one's taste and does not induce microbial resistance. Each member of the Study Group and Control 1 Group applied approximately 30-60 mg of Dental Gel every night after oral hygiene flossing and brushing with toothpaste, applying the same brush on the dental surfaces, and were monitored weekly for the first month and after the 7th, 14th, and 24th week to evaluate plaque and/or tartar development in each of the groups.

Results

In the Study group, the oral gel composition was applied during the trial (10 participants). One of the subjects (10%) developed dentomicrobiana plaque level 1+ in the 7th week of tracking, without increasing the amount of plaque until the end of follow-up. The same participant developed level 1+ tartar in the 24th week of monitoring (Table 1).

In the Control 1 Group, in which the oral dental gel was not applied during the test, five (50%) of the subjects showed dentomicrobiana plaque level 1+ in the 3rd week of tracking. In the fourth week of monitoring, one of these affected individuals developed dentomicrobiana plaque level 2+. Then the number of dentomicrobiana plaque affected individuals increased steadily until reaching 100% at the end of the study (6 with level 1+, and 4 with level 2+). In the third week of monitoring one of the individuals belonging to this group showed tartar level 1+. Then, the number of tartar level 1+ affected individuals increased steadily until reaching 60% in the 24th week of tracking. Not until the 24th week of monitoring, one person developed tartar level 2+.

In the Control 2 Group, one person was affected with level 1+ dentomicrobiana plaque since the first week of monitoring, then, the number of dentomicrobiana plaque affected individuals increased quickly until reaching 100% in the fourth week of monitoring. Also the level 2+ of 24th appeared in 1 individual since the third week of tracking and, their number augmented continuously until 5 in the 24th week of monitoring. One individual belonging to this group was affected with dentomicrobiana plaque level 3+ since the 14th week of monitoring. Tartar level 1+ was formed in 1 person in the week 2, then the number of tartar affected individuals increased continuously until reaching 8 (80%) in the 24th week of tracking (5 with tartar level 1+, 2 with tartar level 2+ and, 1 with tartar level 3+). The results are shown in Table 1.

TABLE 1

Formation of Dentomicrobiana Plaque and Tartar

Study Group

| Week | Dentomicrobiana Plague Level | | | | Tartar Level | | | |
|---|---|---|---|---|---|---|---|---|
| | 0 | 1+ | 2+ | 3+ | 0 | 1+ | 2+ | 3+ |
| 1 | 10 | | | | 10 | | | |
| 2 | 10 | | | | 10 | | | |
| 3 | 10 | | | | 10 | | | |
| 4 | 10 | | | | 10 | | | |
| 7 | 9 | *1* | | | 10 | | | |
| 14 | 9 | *1* | | | 10 | | | |
| 24 | 9 | *1* | | | 9 | *1* | | |

Control Group 1

| Week | Dentomicrobiana Plague Level | | | | Tartar Level | | | |
|---|---|---|---|---|---|---|---|---|
| | 0 | 1+ | 2+ | 3+ | 0 | 1+ | 2+ | 3+ |
| 1 | 10 | | | | 10 | | | |
| 2 | 10 | | | | 10 | | | |
| 3 | 5 | *5* | | | 9 | *1* | | |
| 4 | 5 | *4* | *1* | | 9 | *1* | | |
| 7 | 2 | *7* | *1* | | 8 | *2* | | |
| 14 | 2 | *6* | *2* | | 5 | *5* | | |
| 24 | 0 | *6* | *4* | *1* | 3 | *6* | *1* | |

Control Group 2

| Week | Dentomicrobiana Plague Level | | | | Tartar Level | | | |
|---|---|---|---|---|---|---|---|---|
| | 0 | 1+ | 2+ | 3+ | 0 | 1+ | 2+ | 3+ |
| 1 | 9 | *1* | | | 10 | | | |
| 2 | 8 | *2* | | | 9 | *1* | | |
| 3 | 1 | *8* | *1* | | 9 | *1* | | |
| 4 | 1 | *7* | *2* | | 8 | *2* | | |
| 7 | 0 | *8* | *2* | | 8 | *1* | *1* | |
| 14 | 0 | *7* | *2* | *1* | 2 | *7* | *1* | |
| 24 | 0 | *4* | *5* | *1* | 2 | *5* | *2* | *1* |

Italics: Tartar developing pill

The results obtained in the 3 groups of this clinical trial are striking and confirm that the oral gel composition displays a remarkably protective effect. The oral gel composition produces a slippery mechanical barrier that prevents food debris from adhering to tooth surfaces and to cracks and irregularities in dental organs and to the periodontium. The indigenous flora of the oral cavity on tooth surfaces and periodontium therefore lack sources of nutrients required for growth. Thus, all the harmful consequences that would later result from growth of the indigenous flora in the oral cavity are avoided. At the same time, the traces of ozone contained in the oral gel hinder microbial growth in periodontal tissues and dental organs.

In Group 1 of the study, participants reported a fresh oral cavity and absence of bad breath, which did not occur in groups 2 and 3 (control). At the end of the 24th week, only one participant from the study group showed dental plaque level 1+. No adverse signs or symptoms secondary to the use of the oral gel composition of the present invention were observed. Thus, the oral gel compositions of the present invention provide a mechanical, slick, protective barrier which impedes the formation of plaque without causing any damage.

The results of this trial show that the Dental-Gel is an excellent and effective product that helps achieve oral health by preventing the formation of plaque and reducing dental tartar, cavities and periodontal diseases. The use and application of the oral gel compositions of the present invention under the conditions indicated (supra and subgingival cleaning prior, proper dental hygiene with toothbrush, toothpaste and dental floss), creates the conditions of oral health. The oral gel compositions of the present invention formulation and provide a non-toxic nature almost absolute safety and effectiveness, which greatly promotes use on anyone regardless of their clinical, medical, psychosocial and economic situation. A 30 g tube of the oral gel composition of the present invention (30,000 mg/60 mg per application per day) provides approximately 500 applications making it an affordable investment that enhances the preservation of teeth.

EXAMPLE 3

Preparation of Derma Gel Skin

To create a formulation of the topical gel composition or derma gel, to 15 liters of ozonized water at <20 ppb (<20 µg/l), 105 g of carbopol #940 is added. The carbopol ozonized water is homogenized and allowed to stand for about 24 hours. Subsequently, the solution is polymerized with 50 ml of sodium hydroxide (NaOH/5%), mixed, and 30 ml acetic acid, 30 ml of 3% hydrogen peroxide and 15 g of methyl paraben are added to arrive at the final formulation. About 60 g or 2 oz are produced.

Thus, a preferred formulation of the topical or dermal gel composition of the present invention is: 1) ozonized water; 2) carbopol #940; 3) sodium hydroxide (NaOH); 4) acetic acid; 5) hydrogen peroxide; and 6) methyl paraben.

EXAMPLE 4

Hemostasis Using the Dermal Gel Composition

To evaluate the hemostatic effect of the dermal gel, an experimental rat model was designed. A batch of 45 Wistar rats (bioterio CUIB) were divided into 3 experimental groups of 5 rats c/u. Group No. 1 is Control negative (sterile physiological saline). Group No. 2 is Placebo Control (polymerized carbopol). Group No. 3 is Study "Dermagel".

All rats were administered local anesthetic (sodium pentobarbital 60 mg/kg body weight) and an incision was made immediately in the upper oral periodontium to provoke bleeding, and immediately according to Group sterile physiological saline, placebo or dermagel were added. Blood was collected every minute for a total of 10 minutes. The samples from the incisions were placed on letter-size bond paper and were scanned and a densitometry (Image Analysis Software (ImageJ_Launcher Organization Broken Symmetry Software Version 1.4.3.67) was performed for each batch and group and the corresponding analysis was made.

Hemostasis observed in Group 3 (Dermagel) was less in quantity, less in time and bleeding was inhibited post injury. Generally in the negative control groups (SSF) and placebo, bleeding remained without significant changes in terms of amount of blood and no inhibition of bleeding within 10 minutes of the test. In addition, densitometry showed results for hemostasis in favor of Group 3 (Dermagel). Results are for Group 1 (SSF): 0.866; for Group 2 (Placebo): 0694; and for Group 3 (study-Dermagel): 0.132. Thus, the topical or dermal gel can be used in skin lesions with minimal to moderate bleeding and for other known skin conditions.

EXAMPLE 5

Analgesia Using the Topical or Dermal Gel Compositions

To evaluate the analgesic effect of the topical gel in acute nociceptive pain, the formalin test model was used. The analgesic effects of the topical gel compositions were demonstrated by inducing, via Formalin, a painful stimulus at 2% (50 µl subcutaneously), compared with a negative control solution of physiological sterile saline and positive control of Ketorolac of 100 µg/50 µl. A lot of 24 Wistar rats were used with an average weight of 250 g (bioterio CUIB) and were divided into 3 experimental groups of 8 rats c/u. Group 1 is a positive control: DOLAC® Ketorolac 30 mg/ml, 100 mg/50 ul subcutaneous/left paw, after 30 minutes 50 ml formalin was administered at 2% to the left paw. Group 2 is a negative control: solution saline physiological sterile saline solution, 50 ml via subcutaneous left paw, after 30 minutes 50 ml formalin was administered at 2%/left paw. Group 3 is Dermagel: 50 ml via subcutaneous left paw, after 30 minutes 50 ml formalin was administered at 2%/left paw. Subsequent to formalin injection, painful or nociceptive behavior expressed as a left paw shake/minutes were counted as "zero" minute at 5 minute intervals for 60 minutes.

In the "zero", 5, 10, 55 and 60 minutes of experimentation, the 3 groups showed very similar numbers of left paw shakes. In a time lapse from 15 to 50 minutes, both the positive control Group 1 ketorolac at 100 µg/50 µl and the Group 3 Dermagel showed very similar analgesic properties and the analysis of their T distribution was identical (0.000211555). The negative control Group 2 treated with physiological sterile saline solution in the same time range generally had a greater number of left paw shakes per minute. The T distribution is (0.000006358) and therefore less analgesic compared to the positive control ketorolac Group I and Group 3 Dermagel. These results demonstrate that the topical or dermal gel composition administered subcutaneously has very similar properties to that of the analgesic ketorolac and can be applied topically at least to abrasions, wounds, mild to moderate skin burns with minimal adverse risks.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A biocompatible gel, comprising:
   a formulation of a polymerized cross-linked polyacrylate ozonized water homogenate containing less than 20 µg/l of ozone and a preservative.

2. The biocompatible gel of claim 1, wherein the preservative is methyl paraben.

3. The biocompatible gel of claim 1, wherein said cross-linked polyacrylate is polymerized with sodium hydroxide, acetic acid and hydrogen peroxide.

4. The biocompatible gel of claim 1, wherein said gel is a topical formulation comprising:
   the ozonized water;
   the cross-linked polyacrylate polymer;
   sodium hydroxide;
   acetic acid;
   hydrogen peroxide; and
   the preservative.

5. A topical gel composition, comprising:
   a formulation in ozonized water of cross-linked polyacrylate and methyl paraben, said polyacrylate polymerized in sodium hydroxide, acetic acid and hydrogen peroxide.

6. The oral gel composition of claim 5, wherein the ozonized water contains less than 20 µg/l of ozone.

7. The oral gel composition of claim 5, wherein the formulation contains per liter of ozonized water about 6.3 g to about 7.7 g of the polyacrylate, about 0.7 g to about 1.3 g of the methyl paraben, about 3.0 ml to about 3.7 ml of the sodium hydroxide, about 1.5 ml to about 2.5 ml of the acetic acid, and about 1.5 ml to about 2.5 ml of the hydrogen peroxide.

8. A method for treating an injury to skin on a subject, comprising the step of:
   applying an amount of the topical gel composition of claim 5 to the injury thereby improving hemostasis of the injury and increasing analgesia in the subject.

* * * * *